(12) United States Patent
Hines et al.

(10) Patent No.: US 8,178,106 B2
(45) Date of Patent: May 15, 2012

(54) TOPICAL SKIN CARE FORMULATIONS

(75) Inventors: Michelle Hines, Hickory Creek, TX (US); Tiffany Florence, Dallas, TX (US)

(73) Assignee: Mary Kay Inc., Dallas, TX (US)

( * ) Notice: Subject to any disclaimer, the term of this patent is extended or adjusted under 35 U.S.C. 154(b) by 397 days.

(21) Appl. No.: 12/605,170

(22) Filed: Oct. 23, 2009

(65) Prior Publication Data

US 2010/0247563 A1 Sep. 30, 2010

Related U.S. Application Data

(60) Provisional application No. 61/166,139, filed on Apr. 2, 2009, provisional application No. 61/164,802, filed on Mar. 30, 2009.

(51) Int. Cl.
*A61K 36/06* (2006.01)
*A61K 36/02* (2006.01)
*A61K 36/00* (2006.01)
*A61K 36/55* (2006.01)
*A61K 36/13* (2006.01)

(52) U.S. Cl. ............. 424/195.16; 424/195.17; 424/725; 424/750; 424/768; 424/770

(58) Field of Classification Search ........................ None
See application file for complete search history.

(56) References Cited

U.S. PATENT DOCUMENTS

| | | | | |
|---|---|---|---|---|
| 2,798,053 A | 7/1957 | Brown | ............................. | 521/38 |
| 3,755,560 A | 8/1973 | Dickert et al. | ............. | 514/772.6 |
| 4,421,769 A | 12/1983 | Dixon et al. | .................... | 514/772 |
| 4,509,949 A | 4/1985 | Huang et al. | ........................ | 8/558 |
| 4,599,379 A | 7/1986 | Flesher et al. | ................ | 524/801 |
| 4,628,078 A | 12/1986 | Glover et al. | ............. | 526/303.1 |
| 4,835,206 A | 5/1989 | Farrar et al. | .................... | 524/457 |
| 4,849,484 A | 7/1989 | Heard | ............................. | 525/221 |
| 5,011,681 A | 4/1991 | Ciotti et al. | .................... | 510/136 |
| 5,087,445 A | 2/1992 | Haffey et al. | .................... | 424/59 |
| 5,100,660 A | 3/1992 | Hawe et al. | ................. | 424/78.35 |
| 5,411,744 A | 5/1995 | Hill et al. | ........................ | 424/450 |
| 6,203,802 B1 | 3/2001 | Handjani et al. | ............... | 424/401 |
| 6,387,398 B1 | 5/2002 | Vollhardt et al. | .............. | 424/450 |
| 8,048,456 B2 * | 11/2011 | Burke-Colvin et al. | ....... | 424/725 |
| 2004/0109905 A1 | 6/2004 | Bagchi | ............................ | 424/732 |
| 2005/0163880 A1 | 7/2005 | Pusateri et al. | ................ | 424/777 |
| 2006/0165636 A1 * | 7/2006 | Hasebe et al. | .............. | 424/70.14 |
| 2007/0003536 A1 * | 1/2007 | Zimmerman et al. | ........ | 424/94.4 |
| 2007/0116696 A1 * | 5/2007 | Riley | ............................ | 424/94.5 |
| 2009/0068255 A1 * | 3/2009 | Yu et al. | ......................... | 424/450 |
| 2010/0247563 A1 * | 9/2010 | Hines et al. | .............. | 424/195.16 |
| 2010/0260695 A1 * | 10/2010 | Burke-Colvin et al. | ......... | 424/62 |
| 2011/0044920 A1 * | 2/2011 | Hines et al. | ...................... | 424/60 |
| 2011/0052737 A1 * | 3/2011 | Florence et al. | ............... | 424/742 |
| 2011/0086116 A1 * | 4/2011 | Florence et al. | .............. | 424/739 |
| 2011/0206793 A1 * | 8/2011 | Hines et al. | .................... | 424/769 |

OTHER PUBLICATIONS

Cao et al., "Oxygen-radical absorbance capacity assay for antioxidants," *Free Radical Biology & Medicine*, 14:303-311, 1993.
CTFA International Cosmetic Ingredient Dictionary, 4th edition, pp. 12 and 80, 1991.
Kreuter, "Possibilities of using nanoparticles as carriers for drugs and vaccines," *J. Microencapsulation*, 5:115-127, 1988.
Packman and Gans, "Topical moisturizers: quantifications of their effect on superficial facial lines," *J. Soc. Cosmet. Chem.*, 29:79-90, 1978.

* cited by examiner

*Primary Examiner* — Christopher R. Tate
(74) *Attorney, Agent, or Firm* — Fulbright & Jaworski L.L.P.

(57) ABSTRACT

Disclosed is a topical skin care composition comprising: (a) a combination of the following extracts: *Malpighia punicifolia* (acerola) extract; *Argania spinosa* (argan) extract; *Myrciaria dubia* (camu camu) extract; *Punica granatum* (pomegranate) extract; *Pinus sylvestris* extract; *Terminalia ferdinandiana* (kakadu plum) extract; *Linum usitatissimum* (linseed) extract; *Ribes nigrum* (black current) extract; *Secale cereale* (rye) extract; algae extract; and yeast extract; and (b) a dermatologically acceptable vehicle.

15 Claims, 3 Drawing Sheets

| Extract | Soluble Collagen | Fibronectin | Laminin | Collagen Promoter | Elastin Promoter |
|---|---|---|---|---|---|
| Acerola | 81% | - | 23% | 30-50% | - |
| Argan | - | 33% | 78% | - | >65% |
| Camu-Camu | 236% | 10% | 41% | 50-65% | 15-30% |
| Pomegranate | 67% | - | 32% | 30-50% | 50-60% |
| Epica | 44% | 36% | 80% | 15-30% | - |
| Kakadu | 31% | - | - | 15-30% | - |

FIG. 1

| Inhibition of Enzyme Activity | | | | |
|---|---|---|---|---|
| Extract | MMP 1 | MMP 2 | MMP 3 | MMP 9 |
| Acerola fruit | 20% | - | 48% | 75% |
| Camu-Camu | - | 23% | 43% | 19% |
| Pomegranate | - | - | 63% | 25% |
| Epica | 20.3% | - | 29% | - |
| Flax | - | 28% | 52% | 15% |
| Kakadu | - | - | 15% | 22% |

FIG. 2

| PARAMETER | Biomechanical Tissue Characterization | | | |
|---|---|---|---|---|
| | % Improvement from Baseline | | | |
| | Week 4 | | Week 7 | |
| | cheek | eye | cheek | eye |
| Pliability (Stiffness) | 6% | NS | 21% | 19% |
| Softness (Energy Absorption) | 7% | NS | 22% | 21% |
| Dryness (SEsc – scaliness) | NS | 13% | 15% | 13% |

NS: Not significant at 95% confidence

|  | Week 4 | | Week 7 | |
| --- | --- | --- | --- | --- |
| Facial Attributes | % Improvement N=28 | % of Panelists Showed Improvement | % Improvement N=23 | % of Panelists Showed Improvement |
| *Texture* | 31% | 82% | 29% | 74% |
| *Clarity* | 9% | 46% | 7% | 44% |
| *Fine Wrinkling* | NS | NS | 15% | 61% |
| *Coarse Wrinkling* | 12% | 50% | 24% | 70% |
| *Overall Photodamage* | 11% | 43% | 30% | 87% |

NS; Not significant at 95% confidence

FIG. 5

TOPICAL SKIN CARE FORMULATIONS

CROSS REFERENCE TO RELATED APPLICATIONS

This application claims the benefit of U.S. Provisional Application Ser. No. 61/166,139, filed, Apr. 2, 2009, and U.S. Provisional Application Ser. No. 61/164,802, filed Mar. 30, 2009. The contents of these applications are incorporated by reference.

BACKGROUND OF THE INVENTION

A. Field of the Invention

The present invention relates generally to compositions that can be used to improve the skin's visual appearance. In particular, the present invention concerns topical skin care compositions that include *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof.

B. Description of Related Art

With aging, chronic exposure to adverse environmental factors, or malnutrition, the visual appearance, physical properties, and physiological functions of skin can change in ways that are considered visually undesirable. The most notable and obvious changes include the development of fine lines and wrinkles, loss of elasticity, increased sagging, loss of firmness, loss of color evenness or tone, coarse surface texture, and mottled pigmentation. Less obvious, but measurable changes which occur as skin ages or endures chronic environmental insult include a general reduction in cellular and tissue vitality, reduction in cell replication rates, reduced cutaneous blood flow, reduced moisture content, accumulated errors in structure and function, alterations in the normal regulation of common biochemical pathways, and a reduction in the skin's ability to remodel and repair itself. Many of the alterations in appearance and function of the skin are caused by changes in the outer epidermal layer of the skin, while others are caused by changes in the lower dermis.

For most of the existing skin treatment options that are available, there is a period of time, up to several weeks or months, during which the skin becomes irritated and after which tolerance sets in and the symptoms of irritation may decrease and/or cease.

SUMMARY OF THE INVENTION

The present invention overcomes deficiencies in the art by providing compositions that can be used in skin treatment applications. The compositions of the present invention can include *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof. Further, as shown in the figures and examples (which are incorporated into this section by reference), the inventors have discovered that the combination of anyone of *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine produce synergistic and complimentary effects that are beneficial to skin.

In certain embodiments, the compositions are formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include emulsions (e.g., oil-in-water and water-in-oil emulsions), creams, lotions, solutions (e.g., aqueous or hydro-alcoholic solutions), anhydrous bases (e.g., lipstick or a powder), gels, and ointments. In other non-limiting embodiments, the compositions of the present invention can be included in anti-aging, cleansing, or moisturizing products. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result (e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.). In particular embodiments, the composition has a viscosity ranging from 30,000 to 50,000 cps. The compositions in non-limiting aspects can have a pH of about 6 to about 9. In other aspects, the pH can be 1, 2, 3, 4, 5, 6, 7, 8, 9, 10, 11, 12, 13, or 14. In other aspects, the compositions can be sunscreens having a sun protection factor (SPF) of 1, 5, 10, 15, 20, 25, 30, 35, 40, 45, 50, 55, or more.

In particular aspects, the compositions can be oil-free, substantially anhydrous, and/or anhydrous. Other aspects include compositions having water.

The compositions of the present invention can include from about 0.001% to about 50%, by weight, of *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof. It should be recognized, however, that the amount of such ingredients within a composition can be modified below, within, or above this range based on the desired results. Therefore, the amount of such ingredients can include less than 0.0001%. In other aspects, the compositions can include 0.0001, 0.0002 . . . 0.002, 0.003, 0.004 . . . 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 95, 96, 97, 98, 99%, or more or, or any range derivable therein, by weight or volume of *Argania spinosa* (argan) seed kernel extract, *Secale cereale* (rye) seed extract, *Linum usitatissimum* (linseed) seed extract, *Malpighia*

*punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof.

The compositions of the present invention can also be modified to have a desired oxygen radical absorbance capacity (ORAC) value. In certain non-limiting aspects, the compositions of the present invention can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

In other non-limiting aspects of the present invention, the compositions can further include a vitamin, a mineral, an essential fatty acid, an amino acid, a flavonoid, and/or a protein, or a combination thereof. Non-limiting examples of vitamins include the B vitamins (e.g., B1, B2, B6, B12, niacin, folic acid, biotin, and pantothenic acid), vitamin C, vitamin D, vitamin E (e.g., tocopherol or tocopheryl acetate), vitamin A (e.g., palmitate, retinyl palmitate, or retinoic acid), and vitamin K. Non-limiting examples of minerals include iron, potassium, phosphorus, magnesium, manganese, selenium, and calcium. Non-limiting examples of essential fatty acids include Omega 3 (linolenic acid), Omega 6 (linoleic acid) and Omega 9 (oleic acid) essential fatty acid, or a combination thereof. Non-limiting examples of amino acids include essential amino acids (e.g., lysine, leucine, isoleucine, methionine, phenylalanine, threonine, tryptophan, valine, histidine, or arginine) and non-essential amino acids (e.g., serine, asparagine, glutamine, aspartic acid, glutamic acid, alanine, tyrosine, cysteine, glycine, or proline). Non-limiting examples of flavonoids include anthocyanin compounds (e.g., cyanidin-3-glucoside and cyanidin-3-rutinoside).

The compositions can include a triglyceride, a preservative, an essential oil, a UV absorption ingredient, and/or additional ingredients described in the specification and known in the art, and any combination thereof. Non-limiting examples of triglycerides include small, medium, and large chain triglycerides. Non-limiting examples of preservatives include methylparaben, propylparaben, or a mixture of methylparaben and propylparaben. Non-limiting examples of essential oils are those described in the specification and those known to a person of ordinary skill in the art. Examples include sesame oil, macadamia nut oil, tea tree oil, evening primrose oil, Spanish sage oil, Spanish rosemary oil, Coriander oil, Thyme oil, or Pimento berries oil. Non limiting examples of UV absorption ingredients include dibenzoylmethane derivatives (e.g., avobenzone), octocrylene, oxybenzone, homosalate, octisalate, octyl methoxycinnamate, ecamsule, titanium dioxide, zinc oxide, etc., and others described in the specification and known to those in the art, and any combination thereof.

In other aspects, the compositions of the present invention can include any one of, any combination of, or all of the plant extracts disclosed throughout this specification along with any other cosmetic or pharmaceutical ingredient described in this specification. For instance, the compositions can include any one of, any combination of, or all of the plant extracts in combination with any one of, any combination of, or all of the UV absorbing agents, moisturizing agents, antioxidants, structuring agents, emulsifiers, silicone containing compounds, essential oils, thickening agents, and/or preservatives disclosed in this specification. The amounts of such ingredients can range from 0.0001 to 99% or any range or integer derivable therein as disclosed in this specification.

In particular aspects, there is disclosed a topical skin care composition comprising: (a) a combination of the following plant extracts: *Malpighia punicifolia* (acerola) extract; *Argania spinosa* (argan) extract; *Myrciaria dubia* (camu camu) extract; *Punica granatum* (pomegrannate) extract; *Pinus sylvestris* extract; *Terminalia ferdinandiana* (kakadu plum) extract; and *Linum usitatissimum* (linseed) extract; and (b) a dermatologically acceptable vehicle. The dermatologically acceptable vehicle can include: water; glycerin; dimethicone or cyclomethicone; hydrogenated polydecene; butylene glycol; propylene glycol; and betaine. In certain aspects, the dermatologically acceptable vehicle comprises: at least 60% by weight of water; 3 to 10% by weight of glycerin; 2 to 10% by weight of dimethicone or cyclomethicone; 2 to 10% by weight of hydrogenated polydecene; 0.5 to 3% by weight of butylene glycol; 0.5 to 3% by weight of propylene glycol; and 0.5 to 3% by weight of betaine. In certain aspects, the composition further includes adenosine. The composition can be formulated as a serum, cream, lotion, emulsion, etc. or any other vehicle disclosed throughout this specification. In particular aspects, the composition has a viscosity ranging from 30,000 to 50,000 cps as measured by a Brookfield Viscometer using a TC spindle at 2.5 rpm at 25° C. and a oxygen radical absorbance capacity (ORAC) value per mg of at least about 5.0 to about 25.0. The composition can also include the following plant extracts: algae extract; yeast extract; *Secale cereale* (rye) seed extract; and *Ribes nigrum* (black current) leaf extract. In more particular aspects, the topical skin care composition includes *Malpighia punicifolia* (acerola) fruit extract; *Argania spinosa* (argan) seed kernel extract; *Myrciaria dubia* (camu camu) fruit extract; *Punica granatum* (pomegrannate) fruit extract or sterols; *Pinus sylvestris* bark extract; *Terminalia ferdinandiana* fruit (kakadu plum) extract; and *Linum usitatissimum* (linseed) seed extract. The amount of each plant extract can range from 0.00001 to 99% or any range or integer derivable therein. In particular embodiments, the plant extracts can each be included in the composition in a range from 0.001 to 3% by weight or volume of the composition.

In one embodiment, the topical skin care composition can be any one of the compositions disclosed in Tables 1-5 of this specification. The Table 5 composition is a particular non-limiting formulation.

Also disclosed is a method of treating or preventing a skin condition comprising topical application of a composition comprising *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof, wherein the topical application of the composition treats the skin condition. The method can include topical application of the composition to a portion of skin in need of such composition (e.g., skin having a skin condition), wherein topical application reduces or prevents the skin condition when compared to skin that has a skin condition and that has not been treated with the composition. Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, and other inflammatory skin conditions. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. The skin can be facial skin or non-facial skin (e.g., arms, legs, hands, chest, back, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, or a freckle by topical application of the composition to skin having an age spot, skin discoloration, a freckle, etc.

Also disclosed is a method of treating hyperpigmentation comprising applying the compositions of the present invention to the skin. The method can also comprise identifying a person in need of treating hyperpigmentation. Additional methods contemplated by the inventor include methods for reducing the appearance of an age spot, a skin discoloration, or a freckle, reducing or preventing the appearance of fine lines or wrinkles in skin, or increasing the firmness of skin.

In a particular embodiment there is disclosed a method of reducing the appearance of a skin condition comprising topically applying any one of the compositions described in this specification to the skin condition, wherein topical application of the composition to skin condition reduces the appearance of the skin condition. The skin condition can be any one of those described in this specification. In particular aspects, the skin condition is a fine line or wrinkle, uneven skin tone, or an age spot. The skin condition can be located on facial skin, arm skin, leg skin, chest skin, abdomen skin, back skin etc.

In yet another embodiment there is disclosed a method of increasing the firmness of skin comprising topically applying any one of the compositions described in this specification to skin in need thereof (a non-limiting example of which can be sagging skin, aged skin, skin that has reduced elasticity, skin that has skin cells having inadequate amounts of collage, fibronectin, or laminin or all of such proteins, etc.), wherein topical application of the composition to skin increases the firmness of skin. The composition can be used on facial skin, arm skin, leg skin, chest skin, abdomen skin, back skin, etc.

In still another embodiment there is disclosed a method of increasing collagen, fibronectin, or laminin production in a skin cell comprising topically applying any one of the compositions disclosed in this specification to a skin cell that is in need of collagen, fibronectin, or laminin production, wherein the topical application of the composition to the skin cell increases collagen, fibronectin, or laminin production in the skin cell. Typical skin cells can be found in skin that is aged, damaged by UV radiation, damaged by environmental factors, wrinkles, etc. In certain aspects, collagen, fibronectin, and laminin production are increased in the skin cell.

Compositions comprising *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof can produce synergistic effects. For example, such ingredients can work together synergistically to produce effects that exceed the effects of what would be expected if the extracts were used in separate compositions. Non-limiting synergistic effects include the reduction of internal or external oxidative damage, increased collagen production, reduction in inflammatory responses and the inhibition of melanogenesis.

Compositions comprising *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof, can also act in a complementary fashion. For example, such ingredients can be used to reduce inflammatory responses (e.g., the reduction of inflammatory cytokine production) by certain cytokines that are not reduced, or not as significantly reduced, by other ingredients, and vice-versa.

Also contemplated are kits that includes the compositions of the present invention. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, or an anti-aging product.

The compositions and methods for their use can "comprise," "consist essentially of," or "consist of" any of the ingredients disclosed throughout the specification.

It is contemplated that any embodiment discussed in this specification can be implemented with respect to any method or composition of the invention, and vice versa. Furthermore, compositions of the invention can be used to achieve methods of the invention.

In one embodiment, compositions of the present invention can be pharmaceutically or cosmetically elegant. "Pharmaceutically elegant" and/or "cosmetically elegant" describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

"Dermatologically acceptable carrier, vehicle, or medium" means a carrier, vehicle, or medium into which the active ingredients can be effectively incorporated into. A dermatologically acceptable carrier is design to reduce or avoid undue toxicity, incompatibility, instability, allergic response, and the like, when applied to skin.

"Keratinous tissue" includes keratin-containing layers disposed as the outermost protective covering of mammals and includes, but is not limited to, skin, hair and nails.

A "non-volatile oil" includes those substance that will not evaporate at ordinary or room temperature.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as undissolved colloidal suspensions.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "treating," "inhibiting," or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented below.

FIG. 1. Plant-derived extracts stimulate matrix protein synthesis. Human dermal fibroblasts were treated with each extract (1.0% final conc.) in culture media for 3 days. Cell supernatants were collected and analyzed for the presence of various matrix proteins by ELISA. Measurements were normalized for cellular metabolic activity, as determined by bioconversion of MTS.

FIG. 2. Plant-derived extracts inhibit activity of MMP. Recombinant MMP 2 (gelatinase A), 3 (stromelysin-1), or 9 (gelatinase B) was incubated with 1% solutions of each extract in the presence of a chromogenic substrate. Enzyme activity was measured as absorbance over time. Data is expressed as % inhibition of enzyme activity: (−)=10-30% decrease; (−−)=30-50% decrease; (−−−)=50-100% decrease.

Figures 3, 4:
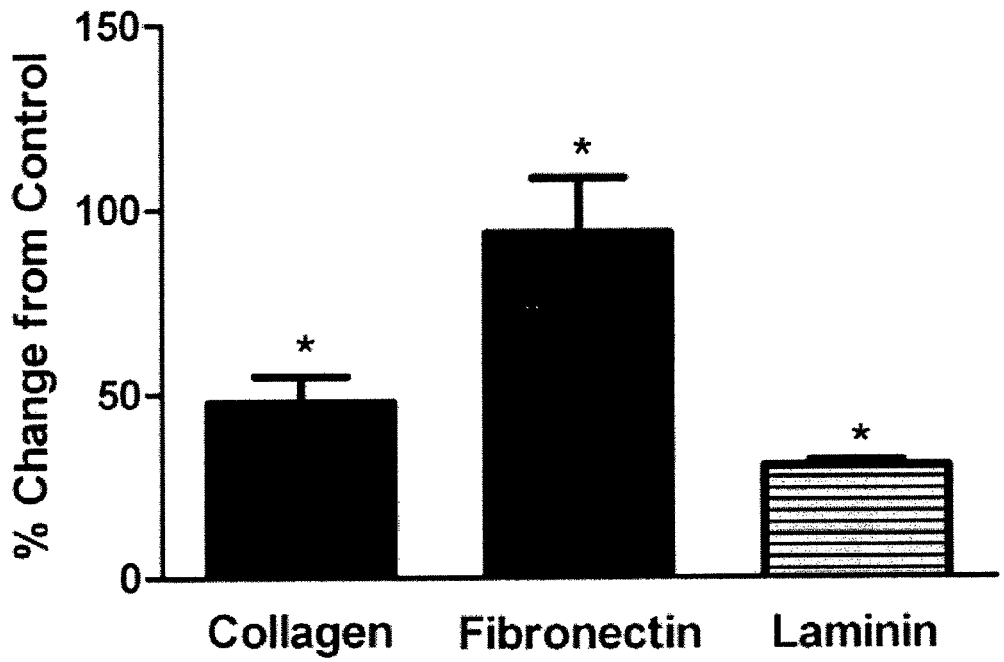
FIG. 3. Topical application of a combined set of extracts stimulates matrix protein synthesis in skin tissue equivalent. Simple cosmetic formulations, with or without plant extracts, were topically applied to skin equivalent tissues. Supernatants were collected following 3 days of treatment and analyzed for the presence of various matrix proteins by ELISA. Data are expressed as % change from formulation control (without plant extracts). (* indicates p<0.05 by unpaired t test.). The combined set of extracts included *Malpighia punicifolia* (acerola) extract; *Argania spinosa* (argan) extract; *Myrciaria dubia* (camu camu) extract; *Punica granatum* (pomegrannate) extract; *Pinus sylvestris* extract; *Terminalia*

*ferdinandiana* (kakadu plum) extract; *Linum usitatissimum* (linseed) extract; *Ribes nigrum* (black current) extract; *Secale cereale* (rye) extract; algae extract; and yeast extract.

FIG. 4. Application of a cosmetic formulation containing the combined set of extracts from FIG. 3 improves facial attributes. A baseline controlled, clinical efficacy study was performed using independent panelists with mild to moderate fine lines and wrinkles. Panelists were evaluated by an expert grader for visual assessments of facial attributes. Overall visual grading improved over baseline at weeks 4 and 7. Remaining attributes, fine wrinkle and coarse wrinkle parameters, showed significant improved at both weeks 4 and 7.

FIG. 5. Biomechanical Tissue Characterization of human skin following application of the formulation from FIG. 5. A baseline controlled, clinical efficacy study performed using independent panelists with mild to moderate fine lines and wrinkles. Panelists were evaluated using the Biomechanical Tissue Characterization (BTC-2000) instrument to assess skin visio-elasticity. Measurements were taken in triplicate from the canthus and cheek area. Pliability, softness and dryness continued to improve at week 7.

DESCRIPTION OF ILLUSTRATIVE EMBODIMENTS

In today's image conscious society, people are continually looking for a product that can improve the visual appearance of their skin. Often times, aged skin, uneven skin tone, or skin damaged by environmental factors such as UV light, chronic sun exposure, environmental pollutants, chemicals, disease pathologies, or smoking, is associated with unattractive skin. Previous attempts to improve the visual appearance of skin has been shown to have various drawbacks such as skin irritation and prolonged recovery periods.

The present invention is an effective alternative to the use of retinoid compounds or other compositions and ingredients currently used to treat aged skin, environmentally-damaged skin, uneven skin tone, and other skin conditions. In one non-limiting aspect, the present invention can be used to improve the skin's visual appearance, physiological functions, clinical properties, or biophysical properties by providing topical skin care formulations that include *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof. These and other aspect of the present invention are described in further detail below.

A. Active Ingredients

As explained above, topical skin care compositions of the present invention can include *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof. These ingredients can be obtained from third party sellers. For instance, *Argania spinosa* (argan) seed kernel extract can be purchased from Laboratories Serobiologiques (France) under the trade name ARGATENSYL LS™ or from Pentapharm/Centerchem (USA) under the trade name REGU-SEB™. *Secale cereale* (rye) seed extract from Silab (France) under the trade names COHELISS™ or MX029-ADAPTINE™ or from Laboratories Serbiologiques (France) under the trade name HSP-BALANCE LS™. *Linum usitatissimum* (linseed) seed extract can be purchased from Lucas Meyer Cosmetics (France) under the trade name LINUMINE™ or from Laboratories Serobiologiques (France) under the trade name ALMONDERMIN LS™. *Malpighia punicifolia* (acerola) fruit extract can be purchased from Greentech S.A. (France) under the trade names ACEROMINE™, ROSAMINE™, or ROSAMINE II™. *Terminalia ferdinandiana* (kakadu plum) extract can be purchased from Southern Cross Botanicals (Australia). *Myrciaria dubia* (camu camu) fruit extract can be purchased from Amax NutraSource (USA) under the trade name CAMU CAMU EXTRACT™ and from Nichirei (Japan) under the trade names CAMU-CAMU EXTRACT B30™ or CAMU-CAMU EXTRACT W™. *Punica granatum* (pomegrannate) fruit extract can be purchased from Active Organics (USA) under the trade names CO ACTIPHYTE OF POMEGRANATE AJ™, CO ACTIPHYTE OF POMEGRANATE GL™, CO ACTIPHYTE OF POMEGRANATE LIPO O™, CO ACTIPHYTE OF POMEGRANATE LIPO RS™, CO ACTIPHYTE OF POMEGRANATE LIPO S™, and CO ACTIPHYTE OF POMEGRANATE LIPO SUN™ *Punica granatum* (pomegrannate) sterols, sterols obtained from pomegrannate fruit and/or seeds, can be purchased from Active Concepts (USA) under the trade name ABS POMEGRANATE STEROLS™. *Pinus sylvestris* bark extract can be purchased from Greentech S.A. (France) under the trade name EPICA™. *Ribes nigrum* (black currant) leaf extract can be purchased from Greentech S.A. (France) under the trade name EPICA™ and from Alban Muller International (France) under the trade names PHYTAMI of ORGANIC BLACKCURRANT™ and BLACKCURRANT LEAF HS™. Palmitoyl oligopeptide, the palmitic acid ester of a synthetic peptide of at least two amino acids selected from alanine, arginine, aspartic acid, glycine, histadine, lysine, proline, serine, or valine, can be purchased from Sederma (France) under the trade names BIO-BUSTYL™, BIO-PEPTIDE-CL™, BIOPEPTIDE-EL™, DERMAXYL™, Haloxyl™, MATRIXYL 3000™, and MAXI-LIP™. Palmitoyl tetrapeptide-7, the reaction product of palmitic acid and tetrapeptide-7 (Gly-Gln-Pro-Arg), can be purchased from Sederma (France) under the trade names EYELISS™, HALOXYL™, MATRIXYL 3000™, and RIGIN™. Adenosine conforms to the following formula and can be purchased from a wide variety of suppliers, including Naturogin Inc. (Korea) and Biospectrum (India):

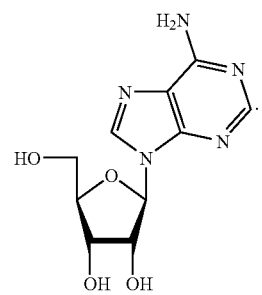

Additional information and suppliers of the above-listed ingredients (and the corresponding trade names) can be found in International Cosmetic Ingredient Dictionary Handbook, 12th Edition (2008), which is incorporated by reference. Further, the extracts identified above can be produced by obtaining the corresponding fruit, seed, or leaf, to produce the extract by extraction methods which are known to those of ordinary skill in the art. The inventors also contemplate that other portions of the substrate (e.g., *argania spinosa* (argan), *Secale cereale* (rye), *Linum usitatissimum* (linseed), *Malpighia punicifolia* (acerola), *Terminalia ferdinandiana* (kakadu plum), *Myrciaria dubia* (camu camu), *Punica granatum* (pomegrannate), *Pinus sylvestris* (Pinus), *Ribes nigrum* (black currant)) producing the extract can be used in the compositions and methods of the present invention. Non-limiting examples of the other portions include the whole fruit, whole vegetable, whole plant, whole tree, whole bush, seed, peel, fruit, stem, bark, leaf, root, flower, petal, bulb, etc. These other portions are described in the International Cosmetic Ingredient Dictionary Handbook, 12th Edition (2008), which is incorporated by reference.

B. Oxygen Radical Absorbance Capacity

Oxygen Radical Absorption (or Absorbance) Capacity (ORAC) is an assay that measures the antioxidant activity of an ingredient or composition. In essence, it can quantify the degree and length of time it takes to inhibit the action of an oxidizing agent such as oxygen radicals that are known to cause damage cells (e.g., skin cells). The ORAC value of the compositions of the present invention can be determined by methods known to those of ordinary skill in the art (see U.S. Publication Nos. 2004/0109905 and 2005/0163880; Cao et al. (1993)), all of which are incorporated by reference). In summary, the assay described in Cao et al. (1993) measures the ability of antioxidant compounds in test materials to inhibit the decline of B-phycoerythrm (B-PE) fluorescence that is induced by a peroxyl radical generator, AAPH.

C. Compositions of the Present Invention

It is contemplated that the compositions of the present invention can include *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof. Additionally, the compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

The disclosed compositions of the present invention may also include various antioxidants to retard oxidation of one or more components. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

D. Vehicles

The compositions of the present invention can be incorporated into all types of vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and agents be selected in such a way that the combinations are chemically compatible and do not form complexes which precipitate from the finished product.

It is also contemplated that ingredients identified throughout this specification, including but not limited to *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof, can be individually or combinatorially encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver the ingredient to skin (see, e.g., U.S. Pat. Nos. 6,387,398; 6,203,802; 5,411,744; Kreuter 1998).

E. Cosmetic Products and Articles of Manufacture

The composition of the present invention can also be used in many cosmetic products including, but not limited to, sunscreen products, sunless skin tanning products, hair products, finger nail products, moisturizing creams, skin benefit creams and lotions, softeners, day lotions, gels, ointments, foundations, night creams, lipsticks, cleansers, toners, masks, or other known cosmetic products or applications. Additionally, the cosmetic products can be formulated as leave-on or rinse-off products. In certain aspects, the compositions of the present invention are stand-alone products.

F. Additional Ingredients

In addition to the *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, and/or adenosine ingredients disclosed throughout this specification, compositions of the present invention can include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraminobenzoic acid ("PABA") and corresponding PABA derivatives, titanium dioxide, zinc oxide, etc.), essential oils, vitamins (e.g. A, B, C, D, E, and K), trace metals (e.g. zinc, calcium and selenium), anti-irritants (e.g. steroids and non-steroidal anti-inflammatories), botanical extracts (e.g. aloe vera, chamomile, cucumber extract, *ginkgo biloba*, ginseng, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, and manitol), exfoliants, waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate). Non-limiting examples of some of these ingredients are provided in the following subsections.

a. UV Absorption Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, alanine, algae extract, aloe barbadensis, aloebarbadensis extract, aloe barbadensis gel, althea officinalis extract, apricot (prunus armeniaca) kernel oil, arginine, arginine aspartate, arnica montana extract, aspartic acid, avocado (*persea gratissima*) oil, barrier sphingolipids, butyl alcohol, beeswax, behenyl alcohol, beta-sitosterol, birch (*betula alba*) bark extract, borage (*borago officinalis*) extract, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, *cardamon* (elettaria cardamomum) oil, carnauba (*copernicia cerifera*) wax, carrot (*daucus carota sativa*) oil, castor (*ricinus communis*) oil, ceramides, ceresin, ceteareth-5, ceteareth-12, ceteareth-20, cetearyl octanoate, ceteth-20, ceteth- 24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, eucalyptus globulus oil, evening primrose (oenothera biennis) oil, fatty acids, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, maltitol, matricaria (*chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium* dulcis) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, sandalwood (*santalum album*) oil, serine, serum protein, sesame (*sesamum indicum*) oil, shea butter (*butyrospermum parkii*), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus* dulcis) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

c. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agent, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

In certain aspects of the present invention, the compositions do not include an emulsifier. In other aspects, however, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

g. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

h. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene or trihydroxystearin, or a mixture of both.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

i. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

G. Kits

Kits are also contemplated as being used in certain aspects of the present invention. For instance, compositions of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Testing Vehicles

Non-limiting examples of compositions of the present invention are described in Tables 1 and 2. These compositions can be used as vehicles to test the efficacy of the active ingredients to treat skin.

TABLE 1*

| Ingredient | % Concentration (by weight) |
| --- | --- |
| Phase A | |
| Water | q.s. |
| Xanthum gum | 0.1 |
| M-paraben | 0.15 |
| P-paraben | 0.1 |
| Citric acid | 0.01 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C | |
| Active Ingredients** | 2.0 |

*Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.

**Any of the active ingredients (or combination thereof) described in the specification can be used. For instance, the active ingredients can include *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof. Although the total amount of active ingredients in the Table 1 formulation is 2% w/w, it is contemplated that the amount of active ingredients can be increased or decreased to achieve a desired result, where the water amount can be increased/decreased accordingly (e.g., q.s.).

TABLE 2*

| Ingredient | % Concentration (by weight) |
|---|---|
| Phase A | |
| Water | q.s. |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |
| Phase B | |
| Sepigel 305 | 2.0 |
| Phase C | |
| Active Ingredient(s)** | 2.0 |

*Add ingredients in phase A to beaker and heat to 70-75° C. while mixing. Subsequently, add the phase B ingredient with phase A and cool to 30° C. with mixing. Subsequently, add phase C ingredient while mixing.

**Any of the active ingredients (or combination thereof) described in the specification can be used. For instance, the active ingredients can include *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof. Although the total amount of active ingredients in the Table 1 formulation is 2% w/w, it is contemplated that the amount of active ingredients can be increased or decreased to achieve a desired result, where the water amount can be increased/decreased accordingly (e.g., q.s.).

Example 2

Non-Limiting Vehicles and Product Formulations

A non-limiting product formulation of the present invention is described in Table 3.

TABLE 3*

| Ingredient** | % Concentration (by weight) |
|---|---|
| *Malpighia punicifolia* (acerola) extract | 0.001 to 3% |
| *Argania spinosa* (argan) extract | 0.001 to 3% |
| *Myrciaria dubia* (camu camu) extract | 0.001 to 3% |
| *Punica granatum* (pomegrannate) extract | 0.001 to 3% |
| *Pinus sylvestris* extract | 0.001 to 3% |
| *Terminalia ferdinandiana* (kakadu plum) extract | 0.001 to 3% |
| *Ribes nigrum* (black current) leaf extract | 0.001 to 3% |
| dermatologically acceptable vehicle | q.s. |

*Composition can be prepared by any known methods in the art. For instance, simple mixing of the plant extracts with a dermatologically acceptable vehicle can be used. A non-limiting example of such a vehicle is illustrated in Table 4.

**In particular embodiments, the plant extracts are *Malpighia punicifolia* (acerola) fruit extract; *Argania spinosa* (Argan) seed kernel extract; *Myrciaria dubia* (Camu Camu) fruit extract; *Punica granatum* (pomegrannate) fruit extract or sterols; *Pinus sylvestris* bark extract; *Terminalia ferdinandiana* (Kakadu Plum) fruit extract; and *Linum usitatissimum* (linseed) seed extract. In other aspects, the following additional plant extracts can be added to the formulation in a concentration range of 0.001 to 3%, by weight, of the total formulation: algae extract; yeast extract; *Secale cereale* (rye) seed extract; and *Linum usitatissimum* (linseed) extract.

A non-limiting dermatologically acceptable vehicle for the plant extracts of the present invention is described in Table 4. This base set of ingredients can be used to create emulsions, creams, lotions, solutions, etc. For instance, the Table 4 vehicle is used in the product formulation described in Table 5.

TABLE 4*

| Ingredient | % Concentration (by weight) |
|---|---|
| Water | at least 60% |
| Glycerin | 3 to 10% |
| Dimethicone or Cyclomethicone (or a mixture) | 2 to 10% |
| Hydrogenated polydecene | 2 to 10% |
| Butylene glycol | 0.5 to 3% |
| Propylene glycol | 0.5 to 3% |
| Betaine | 0.5 to 3% |
| additional cosmetic ingredients | q.s. |

*Composition can be prepared by any known methods in the art. For instance, simple mixing of the ingredients into a container can be used. Alternatively, the hydrophilic ingredients can be heated to 70-75° C. while mixing. Subsequently, the hydrophobic ingredients can be added followed by any additional cosmetic ingredients with subsequent cooling of the mixture to 30° C. with mixing.

A non-limiting product formulation of the present invention is described in Table 5. This formulation is an oil-in-water emulsion, the viscosity of which ranges from 30,000 to 50,000 cps, as measured on a Brookfield Viscometer using a TC spindle at 2.5 rpm at 25° C.

TABLE 5*

| Ingredient | % Concentration (by weight) |
|---|---|
| Water | q.s. |
| Glycerin | 5.135 |
| Dimethicone | 4.600 |
| Hydrogenated Polydecene | 4.500 |
| Butylene Glycol | 1.600 |
| Propylene Glycol | 1.045 |
| Betaine | 1.000 |
| Alcohol | 0.520 |
| PEG-32 | 0.500 |
| Maltodextrin | 0.435 |
| Polyacrylamide | 0.400 |
| Titanium Dioxide | 0.400 |
| Triethanolamine | 0.320 |
| Diazolidinyl Urea | 0.300 |
| Acrylates/C10-30 Alkyl Acrylate Cross Polymer | 0.250 |
| Alcohol Denat. | 0.208 |
| Disodium EDTA | 0.201 |
| *Argania Spinosa* Kernel Extract | 0.200 |
| C13-14 Isoparaffin | 0.200 |
| *Malpighia Punicifolia* (Aceroal) Fruit Extract | 0.200 |
| Urea | 0.150 |
| *Terminal Ferdinandiana* Fruit Extract | 0.127 |
| Glucosamine HCL | 0.125 |
| Methylparaben | 0.1163 |
| Algae Extract | 0.100 |
| Yeast Extract/Extrait De Levure | 0.100 |
| Phenoxyethanol | 0.095250 |
| Lecithin | 0.075 |
| Silanetriol Trehalose Ether | 0.070 |
| *Myrciaria Dubia* Fruit Extract | 0.065 |
| Sodium Cocoyl Glutamate | 0.060 |
| *Secale Cereale* (Rye) Seed Extract | 0.060 |
| Laureth-7 | 0.055 |
| Xantham Gum | 0.050 |
| *Punical Granatum* Extract | 0.039 |
| Propylparaben | 0.032 |
| Guar Hydroxpropyltrimonium Chloride | 0.020 |
| Carbomer | 0.011 |
| *Linum Usitatissimum* (Linseed) Seed Extract | 0.010 |
| *Pinus Sylvestris* Bark Extract | 0.0075 |
| Cetyl Hydroxyethylcellulose | 0.004 |
| *Ribes Nigrum* (Black Currant) Leaf Extract | 0.0025 |
| Rutin | 0.0025 |
| Ethylparaben | 0.002 |
| Sulisobenzone | 0.002 |
| Chlorphenesin | 0.002 |
| Sodium Methylparaben | 0.0013 |

TABLE 5*-continued

| Ingredient | % Concentration (by weight) |
| --- | --- |
| Butylparaben | 0.001 |
| Palmitoyl Oligopeptide | 0.0002 |
| Palmitoyl Tetrapeptide-7 | 0.0002 |

*Composition can be prepared by any known methods in the art. For instance, simple mixing of the ingredients into a container can be used. Alternatively, the hydrophilic ingredients can be heated to 70-75° C. while mixing. Subsequently, the *Argania spinosa* (Argan) seed kernel extract, Secale cereale (rye) seed extract, *Linum usitatissimum* (linseed) seed extract, *Malpighia punicifolia* (acerola) fruit extract, *Terminalia ferdinandiana* (Kakadu Plum) fruit extract, *Myrciaria dubia* (Camu Camu) fruit extract, *Punica granatum* (pomegrannate) fruit extract or sterols, *Pinus sylvestris* bark extract, *Ribes nigrum* (black currant) leaf extract, can be included with subsequent cooling of the mixture to 30° C. with mixing. The remaining ingredients can be added with continuous mixing.

Example 3

Supporting Data

Data supporting the efficacy of the following plant extracts is presented in FIGS. 1-5: *Argania spinosa* (argan) seed kernel extract; *Secale cereale* (rye) seed extract; *Linum usitatissimum* (linseed) seed extract; *Malpighia punicifolia* (acerola) fruit extract; *Terminalia ferdinandiana* (kakadu plum) fruit extract; *Myrciaria dubia* (camu camu) fruit extract; *Punica granatum* (pomegrannate) fruit extract or sterols; *Pinus sylvestris* bark extract; and *Ribes nigrum* (black currant) leaf extract. Note that the testing vehicle used to obtain these data is not disclosed. However, these data can be confirmed by utilizing the testing vehicles described in Tables 1 and 2 of this application and the procedures outlined in Example 4. These data confirm that the plant extracts stimulate synthesis of procollagen, elastin, FN and LM. Several plant extracts inhibit the activity of multiple MMPs. Topical application of a combination of plant-derived extracts stimulates matrix protein synthesis in a tissue equivalent. Application of cosmetic formulation containing plant-derived extracts to human skin improves facial attributes as assessed by expert dermatological grader. Biomechanical characterization of skin following application of formulation containing plant extracts demonstrates improvement in pliability, softness and dryness.

Example 4

Determining Efficacy of the Compositions of the Present Invention

The efficacy of compositions or active ingredients within a given composition of the present inventions can be determined by methods known to those of ordinary skill in the art.

The following are non-limiting procedures that can be used in the context of the present invention. It should be recognized that other testing procedures can be used, including, for example, objective and subjective procedures. The active ingredients (e.g., *Argania spinosa* (argan) seed kernel extract, *Secale cereale* (rye) seed extract, *Linum usitatissimum* (linseed) seed extract, *Malpighia punicifolia* (acerola) fruit extract, *Terminalia ferdinandiana* (kakadu plum) fruit extract, *Myrciaria dubia* (camu camu) fruit extract, *Punica granatum* (pomegrannate) fruit extract or sterols, *Pinus sylvestris* bark extract, *Ribes nigrum* (black currant) leaf extract, palmitoyl oligopeptide, palmitoyl tetrapeptide-7, or adenosine, or any combination thereof) can be tested for their skin efficacy by using the composition vehicles identified in Tables 1 and 2. As noted in these Tables, the active ingredients and concentration ranges can vary.

Skin moisture/hydration can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72C). Three separate impedance readings can be taken on each side of the face, recorded, and averaged. The T5 setting can be used on the impedance meter which averages the impedance values of every five seconds application to the face. Changes can be reported with statistical variance and significance.

Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$.

Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations were made independently by two clinicians and averaged.

Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations were made independently by two clinicians and averaged.

Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: Ra=Standardize roughness; $l_m$=the traverse (scan) length; and y=the absolute value of the location of the profile relative to the mean profile height (x-axis).

In other non-limiting aspects, the efficacy of the compositions of the present invention can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing the compositions and whitening agents of the present invention or with the base alone as a control. Alternatively, an untreated sample of the skin analog can be used as a control.

All of the compositions and/or methods disclosed and claimed in this specification can be made and executed without undue experimentation in light of the present disclosure. While the compositions and methods of this invention have been described in terms of particular embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A topical skin care composition comprising:
   (a) an effective amount of the following extracts: *Malpighia punicifolia* (acerola) extract; *Argania spinosa* (argan) extract; *Myrciaria dubia* (camu camu) extract; *Punica granatum* (pomegranate) extract; *Pinus sylvestris* extract; *Terminalia ferdinandiana* (kakadu plum) extract; *Linum usitatissimum* (linseed) extract; *Ribes nigrum* (black current) extract; *Secale cereale* (rye) extract; algae extract; and yeast extract; and
   (b) a dermatologically acceptable vehicle.

2. The topical skin care composition of claim 1, wherein the dermatologically acceptable vehicle comprises:
   water;
   (ii) glycerin;
   (iii) dimethicone or cyclomethicone;
   (iv) hydrogenated polydecene;
   (v) butylene glycol;
   (vi) propylene glycol; and
   (vii) betaine.

3. The topical skin care composition of claim 2, wherein the dermatologically acceptable vehicle comprises:
   (i) at least 60% by weight of water;
   (ii) 3 to 10% by weight of glycerin;
   (iii) 2 to 10% by weight of dimethicone or cyclomethicone;
   (iv) 2 to 10% by weight of hydrogenated polydecene;
   (v) 0.5 to 3% by weight of butylene glycol;
   (vi) 0.5 to 3% by weight of propylene glycol; and
   (vii) 0.5 to 3% by weight of betaine.

4. The topical skin care composition of claim 3, wherein the composition includes 0.5 to 3.0% by weight of the combination of extracts.

5. The topical skin care composition of claim 1, wherein the composition has a viscosity ranging from 30,000 to 50,000 cps as measured by a Brookfield Viscometer using a TC spindle at 2.5 rpm at 25° C.

6. The topical skin care composition of claim 5, wherein the composition has a an oxygen radical absorbance capacity (ORAC) value per mg of at least about 5.0 to about 25.0.

7. The topical skin care composition of claim 1, wherein the composition is formulated as an oil-in-water emulsion.

8. The topical skin care composition of claim 1, wherein the composition is formulated as a serum.

9. A method of reducing the appearance of a skin condition comprising topically applying the composition of claim 1 to the skin condition, wherein topical application of the composition to skin condition reduces the appearance of the skin condition, wherein the skin condition is a fine line or wrinkle, uneven skin tone, or an age spot.

10. The method of claim 9, wherein the skin condition is located on facial skin.

11. A method of increasing the firmness of skin comprising topically applying the composition of claim 1 to skin in need thereof, wherein topical application of the composition to skin increases the firmness of skin.

12. The method of claim 11, wherein the skin in need thereof comprises a fine line or wrinkle.

13. The method of claim 12, wherein the composition is applied to facial skin.

14. A method of increasing collagen, fibronectin, or laminin production in a skin cell comprising topically applying the composition of claim 1 to a skin cell that is in need of collagen, fibronectin, or laminin production, wherein the topical application of the composition to the skin cell increases collagen, fibronectin, or laminin production in the skin cell.

15. The method of claim 14, wherein collagen, fibronectin, and laminin production are increased in the skin cell.

* * * * *

UNITED STATES PATENT AND TRADEMARK OFFICE
CERTIFICATE OF CORRECTION

Page 1 of 1

PATENT NO. : 8,178,106 B2
APPLICATION NO. : 12/605170
DATED : May 15, 2012
INVENTOR(S) : Michelle Hines et al.

It is certified that error appears in the above-identified patent and that said Letters Patent is hereby corrected as shown below:

In claim 1, column 26, line 35, delete "water" and insert --(i) water-- therefor.

Signed and Sealed this
Tenth Day of July, 2012

David J. Kappos
*Director of the United States Patent and Trademark Office*